United States Patent [19]

Hirano et al.

[11] 4,179,293

[45] Dec. 18, 1979

[54] COLOR PHOTOGRAPHIC LIGHT-SENSITIVE MATERIAL

[75] Inventors: Shigeo Hirano; Keiichi Adachi; Seiki Sakanoue; Takayoshi Kamio, all of Minami-ashigara, Japan

[73] Assignee: Fuji Photo Film Co., Ltd., Minami-ashigara, Japan

[21] Appl. No.: 932,384

[22] Filed: Aug. 9, 1978

[30] Foreign Application Priority Data

Aug. 9, 1977 [JP] Japan .................................... 52-95256

[51] Int. Cl.$^2$ .......................... G03C 1/76; G03C 7/00
[52] U.S. Cl. .................................................. 430/551
[58] Field of Search ............. 96/56, 74, 77, 95, 100 R, 96/99

[56] References Cited

U.S. PATENT DOCUMENTS

| | | | |
|---|---|---|---|
| 2,728,659 | 12/1955 | Loria et al. | 96/56 |
| 2,732,300 | 1/1956 | Thirtle et al. | 96/100 |
| 3,700,453 | 10/1972 | Knechel | 96/74 |
| 3,930,866 | 1/1976 | Oishi et al. | 96/95 |
| 3,982,944 | 9/1976 | Ohi et al. | 96/56 |

*Primary Examiner*—Travis J. Brown
*Attorney, Agent, or Firm*—Sughrue, Rothwell, Mion, Zinn and Macpeak

[57] ABSTRACT

A color photographic light-sensitive material containing at least one hydroquinone compound substituted with one or two tertiary alkyl groups having 15 carbon atoms, or a precursor thereof. The hydroquinone compounds are particularly useful for preventing color fog or color stain which is observed with color photographic light-sensitive materials.

17 Claims, No Drawings

COLOR PHOTOGRAPHIC LIGHT-SENSITIVE MATERIAL

BACKGROUND OF THE INVENTION

1. Field of the Invention

The present invention relates to a color photographic light-sensitive material and, more particularly, to a silver halide color photographic light-sensitive material having improved photographic properties by using an oily alkylhydroquinone.

2. Description of the Prior Art

It is known that "color fog" (or color stain) is observed with color photographic light-sensitive materials of the type which contain color-forming couplers in silver halide photographic light-sensitive emulsions and which are to be developed using a color developing agent such as a p-phenylenediamine, or with color photographic light-sensitive materials of the type which contain compounds capable of releasing diffusible dyes as a result of the redox reaction which occurs on development of silver halide (diffusible dye releasing redox compounds) and which are to be developed using a black and white developing agent such as 1-phenyl-3-pyrazolidone. It has long been known to use various alkylhydroquinones in order to prevent this phenomenon.

For example, U.S. Pat. Nos. 2,728,659, 3,960,570, etc., describe a process of using hydroquinones mono-substituted with straight chain alkyl groups, and U.S. Pat. No. 3,700,453, West German Patent Application (OLS) No. 2,149,789, Japanese Patent Applications (OPI) Nos. 156,438/75, 106,329/74 (The term "OPI" as used herein refers to a "published unexamined Japanese patent application"), etc., describe the process of using hydroquinones mono-substituted with branched chain alkyl groups. On the other hand, hydroquinones di-substituted with straight chain alkyl groups are described in U.S. Pat. Nos. 2,728,659, 2,732,300 (corresponding to British Patent 752,147) and 3,243,294, British Pat. No. 752,146, *Chemical Abstracts*, Vol. 58, 6367h, etc., and hydroquinones di-substituted with branched chain alkyl groups are described in U.S. Pat. Nos. 3,700,453, 2,732,300 and 3,243,294, *Chemical Abstracts*, Vol. 58, 6367h, Japanese Patent Application (OPI) 156,438/75, Japanese Patent Publication No. 21,249/75, etc.

In addition, related descriptions of the use of alkylhydroquinones as color fog-preventing agents are also given in British Pat. Nos. 558,258, 557,750 (corresponding to U.S. Pat. No. 2,360,290), 557,802, 731,301 (corresponding to U.S. Pat. No. 2,701,197), U.S. Pat. Nos. 2,336,327, 2,403,721, 3,582,333, West German Patent Application (OLS) No. 2,505,016 (corresponding to Japanese Patent Application (OPI) No. 110,337/75), and Japanese Patent Application (OPI) No. 4,819/77.

However, disadvantages exist with conventionally employed monoalkylhydroquinones and dialkylhydroquinones. Many of these hydroquinones are difficult to synthesize, since the synthesis thereof involves 2 to 4 steps. Processes involving less steps require that the reactions be conducted at high temperature for a long time, and, thus, are synthetically unfavorable. Some hydroquinone derivatives have such a low molecular weight that they migrate through each layer in a multilayer color photographic light-sensitive material to cause deleterious side effects. Examples of the deleterious side effects are that some hydroquinone derivatives having a low molecular weight cause a decrease in the sensitivity of the silver halide emulsions and that they reduce diffusible dyes or diffusible dye precursors in the color diffusion transfer photographic process where the pH is relatively high during the development processing step whereby the color of the dyes changes. Some other hydroquinone derivatives are disadvantageous because crystallization thereof occurs during or after coating, resulting in a deterioration of the quality of the coating, or are disadvantageous because an oxidation reaction occurs during the coating procedures or during processing with colored by-products being formed.

On the other hand, in the field of producing color photographic light-sensitive materials, in order to obtain color photographs with higher quality, it has recently been strongly desired to develop a novel color fog-preventing agent (or a scavenger for the oxidation product of a developing agent) which more effectively prevents color fog without reducing the photographic sensitivity, which itself does not crystallize and form crystals and which causes an improvement of light fastness of the dye images formed.

SUMMARY OF THE INVENTION

Therefore, an object of the present invention is to provide novel color fog-preventing agents which effectively prevent color fog without reducing photographic sensitivity.

Another object of the present invention is to provide color fog-preventing agents which can be easily synthesized.

A further object of the present invention is to provide liquid color fog-preventing agents which can be advantageously added, as a dispersion, to an aqueous hydrophilic colloid coating composition without using an organic solvent.

Still a further object of the present invention is to provide color fog-preventing agents which do not cause undesirable side effects, for example, a change of color hue even when they are present during processing with a solution of a high pH such as in the color diffusion transfer process.

Still a further object of the present invention is to provide a color photographic light-sensitive material containing the above-described color fog-preventing agent.

These objects are effectively attained with a hydroquinone compound substituted with one or two tertiary alkyl groups having 15 carbon atoms (when two substituents exist, they are present at the 2- and 5-position, or the 2- and 6-position, etc.), or a precursor thereof, and a color photographic light-sensitive material containing at least one of the hydroquinone compounds described above.

DETAILED DESCRIPTION OF THE INVENTION

The term "precursors" as used herein means compounds capable of releasing hydroquinone compounds upon hydrolysis. For example, hydroquinone compounds wherein the hydrogen atom of one or both of the hydroxyl groups in the hydroquinone nucleus are substituted with an acyl group (the term "acyl group" being used herein in the broad sense and including, for example,

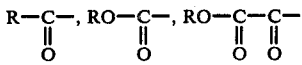

(wherein R represents an aliphatic group such as an alkyl group), etc.).

Suitable hydroquinone compounds of the present invention include compounds represented by the following general formula (I):

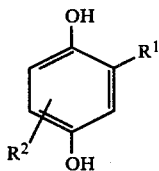

(I)

wherein $R^1$ represents a hydrogen atom,

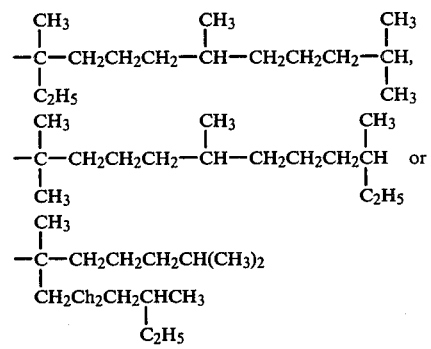

and $R^2$ represents

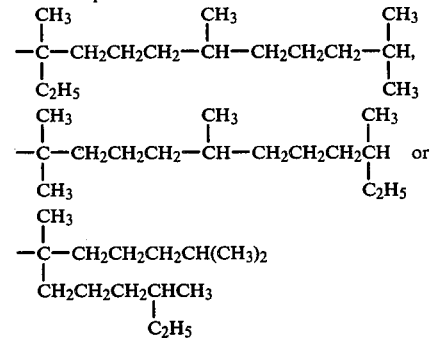

with $R^2$ being present in the 5- or 6-position of the benzene moiety when $R^1$ is not a hydrogen atom. Dialkyl substituted hydroquinone compounds are preferred to monoalkyl substituted hydroquinone compounds.

It is absolutely impossible to expect from the literature described hereinbefore that the hydroquinone compounds of the present invention would show specifically remarkable effects. That is, the hydroquinone compounds of the present invention exhibit, as the specifically remarkable effects, all preferred effects such as high efficiency of preventing color fog (or capturing the oxidation product of a developing agent), improving the light fastness of the dye images, not reducing the sensitivity of silver halide emulsions, less change in color of diffusible dyes when using a development processing solution having a high pH, and not precipitating upon coating or during storage, etc. As a result, the hydroquinone compounds of this invention can be used advantageously to provide excellent color reproduction.

The color fog-preventing agents of the present invention may be used individually or as a combination of two or more thereof in optional proportions, and may also be used in combination with known hydroquinone derivatives described in the literature described hereinbefore. A suitable molar ratio of the color fog-preventing agents of the invention to conventional known hydroquinone derivatives is about 0.1:1 to about 10:1, preferably about 3:1 to about 5:1.

The hydroquinone compounds used in the present invention can be easily prepared, for example, by reacting hydroquinone and 3,7,11-trimethyldodecan-3-ol dissolved in a solvent such as methyl Cellosolve, ethyl acetate or butanol, etc., in the presence of a Lewis acid, such as sulfuric acid, phosphoric acid, etc. More specifically, hydroquinone compounds of this invention can be, in general, prepared by reacting hydroquinone and 3,7,11-trimethyldodecan-3-ol dissolved in a solvent in the presence of a Lewis acid at a temperature of about 0° to about 100° C., preferably of about 30° to about 55° C., for a period of about 2 hours to about 7 hours under atmospheric pressure, preferably in an inert gas such as nitrogen, etc. A suitable concentration of hydroquinone in the solvent is about 0.1 to about 1 g per ml of solvent used, preferably about 0.2 to about 0.5 g per ml of solvent used. A suitable molar ratio of catalyst employed to hydroquinone is about 0.1:1 to about 10:1, preferably about 2:1 to about 4:1. Further, by changing the relative amount of 3,7,11-trimethyldodecan-3-ol to the hydroquinone and by controlling the reaction temperature and the reaction time, a mixture of monoalkyl hydroquinones and dialkyl hydroquinones in an appropriate ratio is obtained. More specifically, in the synthesis of mono-substituted hydroquinone compounds, a suitable molar ratio of hydroquinone to 3,7,11-trimethyldodecan-3-ol is about 1:1.5 to about 1:0.5, preferably about 1:1.1 to 1:0.9. In the synethesis of di-substituted hydroquinone compounds, where $R^1$ is not a hydrogen atom, a suitable molar ratio of hydroquinone to 3,7,11-trimethyldodecan-3-ol is about 1:5 to about 1:1.5, preferably about 1:3 to about 1:2.

The 3,7,11-trimethyldodecan-3-ol used as a starting material can be synthesized as described in *Sekiyugakkaishi*, Volume 17, page 95 (1974), using geranyl acetone as a starting material. Specific examples of the synthesis of the hydroquinone compounds of the present invention are described below. Unless otherwise indicated herein, all parts, percents, ratios and the like are by weight.

Synthesis Example 1

55 g of hydroquinone and 342 ml of 3,7,11-trimethyldodecan-3-ol were dissolved in 100 ml of methyl Cellosolve. Then, 100 ml of concentrated sulfuric acid (36 N) was added dropwise thereto under stirring and cooling so that the temperature did not rise higher than 50° C. Subsequently, the reaction mixture was maintained at 55° to 60° C. for 4 hours. Then, the reaction mixture was added to ice-water, and extracted with 500 ml of benzene. The benzene layer was washed with water and, after drying over anhydrous sodium sulfate, benzene and unreacted 3,7,11-trimethyldodecan-3-ol were distilled off. The residual oily product was distilled under reduced pressure to obtain 245 g of an oily product having a boiling point of 120° to 130° C./0.005 mm Hg. This oily product was determined to be 2,5-bis(1-ethyl- 1,5,9-trimethyldecyl)hydroquinone through elemental analysis and infrared absorption spectral analysis. The oily product was believed to contain a small amount of the 2,6-isomer.

Elemental Analysis Calcd. (%) for $C_{36}H_{66}O_2$: C 81.44 H 12.53. Found (%): C 81.55 H 12.76.

Synthesis Example 2

55 g of hydroquinone and 120 ml of 3,7,11-trimethyldodecan-3-ol were dissolved in 120 ml of methyl Cellosolve. Then, 50 ml of concentrated sulfuric acid (36 N) was added dropwise thereto under stirring and cooling so as to maintain the temperature at 40° C. or less. Subsequently, the reaction mixture was maintained at 50° to 55° C. for 4 hours. The resulting reaction mixture was added to ice-water, and extracted with 500 ml of benzene. The benzene layer was washed with water and, after drying over anhydrous sodium sulfate, benzene and unreacted 3,7,11-trimethyldodecan-3-ol were distilled off under reduced pressure. The residual oil was chromatographed on silica gel using benzene as a developing solvent. Thus, 41 g of 2,5-bis(1-ethyl-1,5,9-trimethyldecyl)hydroquinone (the same compound as obtained in Synthesis Example 1) was first eluted, and then 20 g of 2-(1-ethyl-1,5,9-trimethyldecyl)hydroquinone was eluted. The results of elemental analysis of the above-described monoalkyl hydroquinone are shown below.

Elemental Analysis Calcd. (%) for $C_{21}H_{36}O_2$: C 78.69 H 11.32. Found (%): C 78.40 H 11.51.

2,5-bis(1-Ethyl-1,5,9-trimethyldecyl)hydroquinone and 2-(1-ethyl-1,5,9-trimethyldecyl)hydroquinone were produced in Synthesis Example 2 described above in a weight proportion of about 2:1. The effects of the present invention can be obtained using this mixture as such.

In addition, mass spectral data suggest that the alkyl hydroquinones obtained in Synthesis Examples 1 and 2 contain isomers thereof wherein the alkyl group is a 1,1,5,9-tetramethylundecyl group or a 2,6,10-trimethyl-6-decyl group in place of a 1-ethyl-1,5,9-trimethyldecyl group.

The color fog-preventing agent according to the present invention can be incorporated in a layer of a light-sensitive material, such as a photographic silver halide emulsion layer (in particular, a blue-sensitive silver halide emulsion layer, a green-sensitive silver halide emulsion layer or a red-sensitive silver halide emulsion layer) or an adjacent layer thereto (for example, an interlayer), or a light reflecting layer, etc.

The amount of the color fog-preventing agent to be used will vary depending upon factors such as the end-use of the light-sensitive material, the dye image-providing materials present such as dye image-forming couplers or diffusible dye-releasing redox compounds, the silver halide emulsions employed, the layer structure of the light-sensitive material used, the development processing used, etc. However, generally speaking, a suitable amount of the color fog-preventing agent is about 0.1 to about 150% by weight, particularly 0.2 to 20% by weight, based on the dye image-providing material when the color fog-preventing agent is added to a layer containing the dye image-providing material, or about 1 to about 1,000% by weight, particularly 10 to 400% by weight, based on the dye image-providing material when the color fog-preventing agent is added to a layer other than a layer containing the dye image-providing material.

Where the color fog-preventing agent and the dye image-providing material are incorporated into the same layer, the color fog-preventing agent may be emulsified and dispersed together with the dye image-providing material, or may be emulsified and dispersed separately from the dye image-providing material.

The color photographic light-sensitive material of the present invention is preferably a multilayer multi-color photographic light-sensitive material comprising a support having thereon three silver halide emulsion layers, each sensitive to different spectral wavelength regions. One illustrative example of such a color light-sensitive material is one which comprises a support having thereon a red-sensitive silver halide emulsion layer containing a cyan color-forming coupler, a green-sensitive silver halide emulsion layer containing a magenta color-forming coupler, a blue-sensitive silver halide emulsion layer containing a yellow color-forming coupler and, if desired, light-insensitive auxiliary layers, such as a protective layer, a filter layer, interlayers, an antihalation layer, etc.

The stratal structure of the photographic emulsion layer can comprise a red-sensitive silver halide emulsion layer, a green-sensitive silver halide emulsion layer and a blue-sensitive silver halide emulsion layer in this order from the support, or can comprise a blue-sensitive silver halide emulsion layer, a green-sensitive silver halide emulsion layer and a red-sensitive silver halide layer in this order from the support.

Another illustrative example of such a color light-sensitive material is a film unit comprising a combination of a light-sensitive element represented by a light-sensitive silver halide emulsion layer and an image-receiving element represented by a mordanting layer. In a preferred embodiment, the film unit comprises a transparent support having coated thereon a mordanting layer, a substantially opaque light reflecting layer (for example, a layer containing $TiO_2$ or the combination of a layer containing $TiO_2$ and a layer containing carbon black), a layer comprising a cyan dye-releasing redox compound, a red-sensitive silver halide emulsion layer, an interlayer, a layer comprising a magenta dye-releasing redox compound, a green-sensitive silver halide emulsion layer, an interlayer, a layer comprising a yellow dye-releasing redox compound, a blue-sensitive silver halide emulsion layer and a protective layer and, if desired, other light-insensitive layers. Further, the film unit can include a rupturable container retaining an alkaline processing composition and an opacifying agent, and the container is positioned at one edge of the above-described protective layer or a cover sheet superimposed over the protective layer.

The color fog-preventing agent according to the present invention exhibits superior effects when used in combination with compounds capable of improving light fastness such as with phenolic compounds having an ether bond in the 4-position as described in U.S. Pat. No. 3,930,866 or α-tocopherol acetate described in U.S. Pat. No. 4,015,990. A suitable molar ratio of the color fog-preventing agent of the present invention to such a light fastness increasing compound ranges from about 0.1:1 to about 10:1, preferably 0.2:1 to 5:1.

The dye image-providing materials which can be used in the present invention include conventional dye image-forming couplers, diffusible dye-releasing redox compounds (DRR compounds), diffusible dye-releasing couplers (DDR couplers), and the like.

Non-diffusing couplers having a hydrophobic group called a ballast group in the molecule are preferred as such couplers. Either 4-equivalent or 2-equivalent couplers may be used. However, 2-equivalent couplers are particularly preferred. Also, colored couplers for color correction or couplers capable of releasing a development inhibitor upon development (DIR couplers) may be used together with the dye image-providing materials. Couplers producing colorless coupling reaction products may also be used.

Known open chain ketomethylene couplers can be used as yellow color-forming couplers. Of these, benzoylacetanilide compounds and pivaloylacetanilide compounds are advantageous. Specific examples of usable yellow color-forming couplers are described in U.S. Pat. Nos. 2,875,057, 3,265,506, 3,408,194, 3,551,155, 3,582,322, 3,725,072, 3,891,445, West German Pat. No. 1,547,868, West German Patent Applications (OLS) Nos. 2,213,461, 2,219,917, 2,261,361, 2,263,875, 2,414,006, 2,406,087, etc.

Pyrazolone compounds, indazolone compounds, cyanoacetyl compounds, etc., can be used as magenta color-forming couplers. In particular, pyrazolone compounds are advantageous. Specific examples of usable magenta color-forming couplers are described in U.S. Pat. Nos. 2,600,788, 2,983,608, 3,062,653, 3,127,269, 3,311,476, 3,419,391, 3,519,429, 3,558,319, 3,582,322, 3,615,506, 3,834,908, 3,891,445, 3,935,016, West, German Pat. No. 1,810,464, West German Patent Applications (OLS) Nos. 2,408,665, 2,417,945, 2,418,959, 2,424,467, Japanese Patent Publication No. 6,031/65, etc.

Phenolic compounds, naphtholic compounds, etc., can be used as cyan color-forming couplers. Specific examples thereof are described in U.S. Pat. Nos. 2,369,929, 2,434,272, 2,474,293, 2,521,908, 2,895,826, 3,034,892, 3,311,476, 3,458,315, 3,476,563, 3,583,971, 3,591,383, 3,767,411, West German Patent Applications (OLS) Nos. 2,414,830, 2,454,329, Japanese Patent Application (OPI) No. 59,838/73.

Those colored couplers as described in, e.g., U.S. Pat. Nos. 3,476,560, 2,521,908, 3,034,892, Japanese Patent Publications Nos. 2,016/69, 22,335/63, 11,304/67, 32,461/69, Japanese Patent Application No. 118,029/75, West German Patent Applications (OLS) Nos. 2,418,959, 2,538,323, etc., can be used.

Those DIR couplers as described in, e.g., U.S. Pat. Nos. 3,227,554, 3,617,291, 3,701,783, 3,790,384, 3,632,345, West German Patent Applications (OLS) Nos. 2,414,006, 2,454,301, 2,454,329, British Pat. No. 953,454, Japanese Patent Application No. 146,570/75, etc., can be used.

The light-sensitive material may contain a compound capable of releasing a development inhibitor upon development other than a DIR coupler. For example, those compounds which are described in U.S. Pat. Nos. 3,297,445, 3,379,529, West German Patent Application (OLS) No. 2,417,914, etc., can be used.

Those DDR couplers as described in, e.g., British Pat. Nos. 840,731, 904,364, 932,272, 1,014,725, 1,038,331, 1,066,352 and 1,097,064, Japanese Patent Application (OPI) No. 133,921/76, U.S. Defensive Publication No. T-900,029, U.S. Pat. No. 3,227,559, etc., can be used.

Two or more of the above-described couplers may be incorporated in the same layer, or the same layer coupler may be incorporated in two or more different layers.

Those DDR compounds as described in, e.g., U.S. Published Application No. B-351,673, U.S. Pat. Nos. 3,932,381, 3,928,312, 3,931,144, 3,954,476, 3,929,760, 3,942,987, 3,932,380, 4,013,635 and 4,013,633, Japanese Patent Applications (OPI) Nos. 113,624/76, 109,928/76, 104,343/76 and 4,819/77, Japanese Patent Application No. 64,533/77, Research Disclosure, No. 15157, pp. 68 to 74 (November, 1976) and ibid., No. 13024, pp. 37 to 42 (February, 1975), etc., can be used.

In order to incorporate the dye image-providing materials into a silver halide emulsion layer or an adjacent layer thereto, known processes such as those described in U.S. Pat. No. 2,322,027 are suitable. Examples of such processes are as follows:

(1) A process comprising dissolving a dye image-providing material in an organic solvent which is scarcely miscible with water and which has a high boiling point (not lower than about 170° C.) such as an alkyl phthalate (e.g., dibutyl phthalate, dioctyl phthalate, etc.), a phosphoric acid ester (e.g., diphenyl phosphate, triphenyl phosphate, tricresyl phosphate, dioctylbutyl phosphate, etc.), a citric acid ester (e.g., tributyl acetylcitrate, etc.), a benzoic acid ester (e.g., octyl benzoate, etc.), an alkylamide (e.g., diethyllaurylamide, etc.), a phenol (e.g., p-n-nonylphenol, 2-methyl-4-n-octylphenol, etc.), dispersing this dye image-providing material solution in an aqueous medium to form a dispersion, and mixing this dispersion with a photographic emulsion or a coating solution for a layer adjacent to a photographic emulsion layer.

(2) A process comprising dissolving a dye image-providing material in an organic solvent which is comparatively difficultly miscible with water and which has a low boiling point, dispersing this dye image-providing material solution in an aqueous medium to form a dispersion, and mixing this dispersion with a photographic emulsion or a coating solution for a layer adjacent to a photographic emulsion layer. The organic solvent used is removed during the steps of producing the light-sensitive material. Examples of suitable organic solvents which can be used for this process include ethyl acetate, cyclohexanone, β-n-butylethoxyethyl acetate, etc.

(3) A process comprising dissolving a dye image-providing material in an organic solvent which is readily miscible with water, and adding this dye image-providing material solution to a photographic emulsion, or a coating solution for a layer adjacent to a photographic emulsion layer. The organic solvent used may be either removed during the steps of producing the light-sensitive material or left in the emulsion layer. Illustrative organic solvents suitable for this process include dimethylformamide, dimethyl sulfoxide, N-methylpyrrolidone, glycerin, tetrahydrofuran, diethylene glycol monoacetate, diacetone alcohol, acetonitrile, methyl isobutyl ketone, etc.

(4) A process comprising dissolving a dye image-providing material in an alkaline aqueous solution, and adding this dye image-providing material solution to a photographic emulsion.

Organic solvents used for processes (1), (2) and (3) may be appropriately mixed and then used depending upon the solubility of dye image-providing materials. Also, organic solvents used for processes (3) and (4) may be appropriately mixed and used. A hydrophilic high molecular weight material may be incorporated in the aqueous medium in which the organic solvent solution of the dye image-providing material is to be dispersed. Such hydrophilic high molecular weight materials desirably are quite compatible with the hydrophilic binder in the photographic emulsion, with which this dye image-providing material dispersion is to be mixed. Suitable compounds can be selected from those materials which are used as binders for photographic emulsions.

The dye image-providing materials are generally employed in an amount of about $2\times10^{-3}$ mol to about .2 mol, preferably $1\times10^{-2}$ mol to $5\times10^{-1}$ mol, per mol of silver in the silver halide emulsion layer.

A wide range of supports heretofore known for photographic use can be used as the support to be used for the light-sensitive material of the present invention. For example, synthetic resin film bases such as cellulose acetate, polycarbonate, polyethylene terephthalate, polystyrene, etc., baryta-coated paper, polyethylene laminated paper, glass plates, etc., can be used.

Hydrophilic colloids which can be used for the light-sensitive material of the present invention are high molecular weight materials capable of forming a coating and permeable to a development processing solution. All hydrophilic colloids thus far used for photographic use can be employed in this invention. For example, gelatin, acylated gelatin, graft gelatins, polyvinyl alcohol, polyacrylic acid salts, polyacrylamide, partially hydrolyzed products of polyvinyl acetate, polyacrylamides having been subjected to the Hofmann reaction, acrylic acid/acrylamide/N-vinylimidazole copolymers, polyvinylpyrrolidone, sodium alginate, etc., can be employed.

The hydrophilic colloidal layers of the color light-sensitive material of the present invention, in particular the gelatin-containing layers, can be hardened with various cross-linking agents. For example, cross-linking agents of the non-aldehyde type such as polyoxy compounds described in Japanese Patent Publication No. 7,133/59, poly(1-aziridinyl) compounds described in Japanese Patent Publication 8,790/62, and active halogen compounds described in U.S. Pat. Nos. 3,362,827 and 3,325,287 are particularly useful for the color light-sensitive material of the present invention, although inorganic compounds (e.g., chromium salts, zirconium salts, etc.) and cross-linking agents of the aldehyde type such as mucochloric acid, 2-phenoxy-3-chloromaleinaldehyde acid described in Japanese Patent Publication No. 1,872/71 can in many cases also be usefully employed in the present invention.

The silver halide emulsion to be used for the light-sensitive material of the present invention can be selected from a wide range of emulsions heretofore known depending on the end-use of the light-sensitive material. Suitable silver halides include silver chloride, silver chlorobromide, silver bromide, silver chlorobromoiodide, etc. These photographic emulsions may be sensitized through chemical sensitization such as sulfur sensitization, gold sensitization, reduction sensitization, etc. Furthermore, these emulsions may be stabilized with a slightly soluble silver salt-forming agent such as a mercapto compound (e.g., 1-mercapto-5-phenyltetrazole, etc.) and a stabilizer such as 5-methyl-6-hydroxy-1,3,4-triazaindolizine, etc. Also, the emulsions may contain sensitizing dyes such as cyanines and merocyanines. Commonly used negative type silver halide emulsions (i.e., surface latent image type), non-surface latent image type silver halide emulsions such as direct reversal emulsions (e.g., internal latent image-forming type silver halide emulsions containing an electron-trapping agent, solarization type silver halide emulsions, etc.) can also be used.

The photographic light-sensitive material of the present invention can be used for many purposes. For example, it can be used for color positive films, color print papers, color negative films, color reversal films, film units for the color diffusion transfer process, etc.

In one embodiment, the color photographic light-sensitive material of the present invention is processed, after image-wise exposure, using conventional processes to form color images. The main steps in the processing are color development, bleaching and fixing. If desired, steps such as washing with water, stabilizing, etc., may also be employed. Two or more of these steps may be conducted in the same bath such as a bleach-fixing bath, if desired.

The color development is usually carried out in an alkaline solution containing an aromatic primary amine developing agent. Examples of aromatic primary amine developing agents include p-phenylenediamine type developing agents. Typical examples of these developing agents include 4-amino-3-ethoxy-N,N-diethylaniline, 4-amino-3,5-dimethyl-N,N-diethylaniline, 4-amino-3-methyl-N-ethyl-N-($\beta$-hydroxyethyl)aniline, 4-amino-3-methyl-N,N-diethylaniline, 4-amino-3-methyl-N-ethyl-N-($\beta$-methylsulfonamidoethyl)aniline, 4-amino-3-($\beta$-methylsulfonamidoethyl)-N,N-diethylaniline, 4-amino-N-ethyl-N-($\beta$-hydroxyethyl)aniline, 4-amino-N,N-diethylaniline, 4-amino-N-ethyl-N-$\omega$-sulfobutylaniline, etc.

Suitable bleaching and fixing techniques which can be used in processing the light-sensitive material of this invention are described in U.S. Pat. Nos. 3,994,729, 3,996,055, and 3,997,348.

Further, in another embodiment wherein the color photographic light-sensitive material of the present invention is a film unit for a color diffusion transfer photographic process as described above, the processing is automatically conducted in the film unit. Examples of developing agents which can be retained in a rupturable container include N-methylaminophenol, 1-phenyl-3-pyrazolidone, 1-phenyl-4,4-dimethyl-3-pyrazolidone, 1-phenyl-4-methyl-4-hydroxymethyl-3-pyrazolidone, N,N-diethyl-p-phenylenediamine, 3-methoxy-N,N-diethyl-p-phenylenediamine, etc.

The following examples are given to illustrate the present invention in greater detail.

EXAMPLE 1

200 mg of Color Fog-Preventing Agents (1) and (2) of the present invention synthesized in Synthesis Example 2 above and Comparative Color Fog-Preventing Agents (3) to (8) described below were respectively dissolved in a mixed solvent of 50 mg of di-butyl phthalate and 200 mg of ethyl acetate at about 80° C., and left at 5° C. for 24 hours to compare the degree of precipitation. As a result, large amounts of Comparative Color Fog-Preventing Agents (5) and (6) precipitated, and some precipitation was observed with Comparative Color Fog-Preventing Agents (3), (4), (8) and (7). On the other hand, no formation of crystals of Color Fog-Preventing Agents (1) and (2) in accordance with the present invention was observed.

Color Fog-Preventing Agents (1) The hydroquinone compound substituted with one tertiary alkyl group having 15 carbon atoms synthesized in Synthesis Example 2 above (a mixture of isomers).

(2) The hydroquinone compound substituted with two tertiary alkyl groups having 15 carbon atoms synthesized in Synthesis Example 2 above (a mixture of isomers).

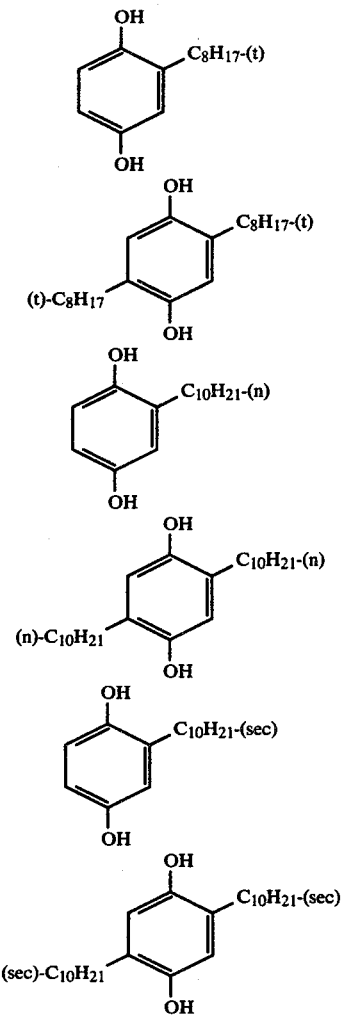

EXAMPLE 2

Emulsified Dispersion A (in accordance with the present invention) having the following composition and Emulsified Dispersions B to D (for comparison) were prepared.

| Emulsified Dispersion Composition A | |
|---|---|
| Gelatin (10% aq. soln.) | 100 ml |
| Di-n-butyl Phthalate | 5 g |
| Color Fog-Preventing Agent | 10 g |
| 2,3-Dihydroxynaphthalene | 0.2 g |
| Sodium Dodecylbenzenesulfonate (5% aq. soln.) | 5 ml |
| Ethyl Acetate | 10 ml |

Dispersion A contained Color Fog-Preventing Agent (2) synthesized in Example 1 as the color fog-preventing agent.

Dispersions B and C contained Color Fog-Preventing Agents (4) and (6) described in Example 1, respectively. Dispersion D did not contain any color fog-preventing agent.

Each of these Dispersions A to D was stored for 4 weeks at 5° C., and filtered using a filter with a pore size of 3μ to examine the amount of crystal formation. Precipitation of crystals was observed with Dispersions B and C, but no precipitation was observed with Dispersions A and D.

EXAMPLE 3

A paper support with polyethylene layers laminated on both sides of thereof was coated with First Layer (as the lowermost layer) to the Sixth Layer (as the upper most layer) described below to prepare a multilayer color light-sensitive material. (In the following table, the amount in mg/m² represents the amount coated.)

| | | |
|---|---|---|
| Sixth Layer (protective layer) | Gelatin | 1,500 mg/m² |
| Fifth Layer (red-sensitive layer) | Silver Chlorobromide Emulsion (AgBr: 50 mol%; 300 mg silver/m² | |
| | Gelatin | 1,500 mg/m² |
| | Cyan Coupler *1 | 500 mg/m² |
| | Coupler Solvent *2 | 250 mg/m² |
| Fourth Layer (UV-light absorbing layer) | Gelatin | 1,200 mg/m² |
| | UV Light-Absorbing Agent *3 | 1,000 mg/m² |
| | Solvent for UV Light-Absorbing Agent *2 | 250 mg/m² |
| Third Layer (green-sensitive layer) | Silver Chlorobromide Emulsion (AgBr: 50 mol%; 450 mg silver/m²) | |
| | Gelatin | 1,500 mg/m² |
| | Magenta Coupler *4 | 400 mg/m² |
| | Coupler Solvent *5 | 200 mg/m² |
| Second Layer | Gelatin | 1,000 mg/m² |
| First Layer | Silver Chlorobromide Emulsion (AgBr: 80 mol%; 450 mg silver/m² | |
| | Gelatin | 1,500 mg/m² |
| | Yellow Coupler *6 | 500 mg/m² |
| | Coupler Solvent *7 | 500 mg/m² |
| Support | Polyethylene Laminated Paper | |

*1 Cyan Coupler: 2-[α-(2,4-Di-t-amylphenoxy)butanamido]-4,6-dichloro-5-methylphenol
*2 Coupler Solvent: Di-n-butyl phthalate
*3 UV Light-Absorbing Agent: 2-(2-Hydroxy-3-sec-butyl-5-t-butyl-phenyl)benzotriazole
*4 Magenta Coupler: 1-(2,4,6-Trichlorophenyl)-3-(2-chloro-5-tetradecanamido)anilino-2-pyrazolin-5-one
*5 Coupler Solvent: o-Cresyl phosphate
*6 Yellow Coupler: α-Pivaloyl-α-(2,4-dioxo-5,5'-dimethyl-oxazolidin-3-yl)-2-chloro-5-[(α-2,4-di-t-amylphenoxy)butanamido]acetanilide
*7 Coupler Solvent: o-Dioctylbutyl phosphate To the Second Layer of the above-described sample was added each of Emulsion Dispersions A, B, C and D prepared as described in Example 2 in an amount of 100 mg/m² of the color fog-preventing agent to obtain Samples (i) to (iv).

Each sample was subjected to ½ second exposure to blue light, green light and red light through a continuous wedge, and to the following processings.

| Step | Time | Temperature |
|---|---|---|
| Color Development | 3 min 30 sec | 31° C. |
| Bleach-Fixing | 1 min 30 sec | " |
| Washing | 2 min | " |
| Drying | | |

The processing solutions used had the following compositions.

| Composition of the Color Developer | |
|---|---|
| Benzyl Alcohol | 15 ml |
| Sodium Sulfite | 5 g |
| Potassium Bromide | 0.5 g |
| Hydroxylamine Sulfate | 2.0 g |
| Sodium Carbonate | 30.0 g |
| Sodium Nitrilotriacetate | 2.0 g |
| 4-Amino-3-methyl-N-(β-methanesulfonamido)-ethylaniline | 5.0 g |
| Water to make | 1,000 ml (pH 10.1) |
| Composition of the Bleach-Fixing Solution | |
| Ammonium Thiosulfate | 105 g |
| Sodium Sulfite | 2 g |
| Disodium Ethylenediaminetetraacetate | 40 g |
| Sodium Carbonate (monohydrate) | 5 g |
| Water to make | 1,000 ml (pH 7.0) |

Separately, Sample (v) comprising a polyethylene laminated paper support having coated thereon only the First Layer (blue-sensitive layer) and the Sixth Layer (protective layer), and Sample (vi) comprising a polyethylene laminated paper having coated thereon only the Third Layer (green-sensitive layer) and the Sixth Layer (protective layer) were prepared, and exposed and developed in the same manner as described above for Samples (i) to (iv). The green density and blue density of the thus-obtained samples were measured using an automatic recording densitometer produced by the Fuji Photo Film Co., Ltd. (Model FAD). The results set forth in Table 1 below were obtained.

Table 1

| | Sample | | | |
|---|---|---|---|---|
| | (i) | (ii) | (iii) | (iv) |
| G → B Stain | 0.06 | 0.10 | 0.12 | 0.16 |
| B → G Stain | 0.01 | 0.03 | 0.06 | 0.11 |

In Table 1 above, G→B Stain means the value obtained by comparing the magenta color component of the maximum yellow color density of the multilayer sample with that of the yellow monolayer colored Sample (v). The smaller the value is, the smaller is the degree of stain. Similarly, B→G Stain means the relative value of the yellow color component in the magenta color density. From the results, it was found that Sample (i) using the color fog-preventing agent of the present invention showed a marked color stain-preventing effect and the color purity of each layer was maintained at a high level.

Furthermore, precipitation of crystals which occurred before, during or after the coating step was observed with Samples (ii) and (iii) using color fog-preventing agents outside the scope of the present invention, whereas precipitation of crystals was not observed at any time with Sample (i) using the color fog-preventing agent of the present invention. It can be seen from this that the property of the dispersion of the present invention as being extremely stable is quite valuable for incorporating color fog-preventing agents in such incorporated-coupler type color light-sensitive materials.

EXAMPLE 4

Samples (i) and (ii) prepared as described in Example 3 were exposed to blue light, green light and red light through a continuous wedge, and subjected to the same development processings as described in Example 3. Each of the resulting samples was irradiated with light for 24 hours using a Fade-Ometer to test light fastness. The degree of reduction in density after the test as compared with a density of 1.5 before the test was measured. The results obtained are shown in Table 2 below.

Table 2

| | REduction in Density | |
|---|---|---|
| Color Image | Sample (i) | Sample (ii) |
| Yellow (blue-sensitive layer) | 0.23 | 0.30 |
| Magenta (green-sensitive layer) | 0.27 | 0.31 |
| Cyan (red-sensitive layer) | 0.10 | 0.10 |

From the results, Sample (i) of the present invention was found to have improved light fastness of yellow and magenta color images as compared with comparative Sample (ii) using Color Fog-Preventing Agent (4) described above, heretofore used as a color fog-preventing agent.

EXAMPLE 5

On a cellulose triacetate film support were coated, in sequence, the following layers to prepare Control Sample (vii).

Control Sample (vii)

First Layer: Red-sensitive silver halide emulsion layer

A layer provided by coating a red-sensitive gelatino-silver bromoiodide highly sensitive emulsion (AgI content: 5 mol%; weight ratio of silver to gelatin: 1/1.5) in a silver amount of 30 mg/100 cm$^2$ and a cyan color coupler in a coupler amount of 6.8 mg/100 cm$^2$. (Thickness*: 3μ)

Second Layer: Interlayer

A layer mainly comprising gelatin. (Thickness: 1μ)

Third Layer: Green-sensitive silver halide emulsion layer

A layer provided by coating a green-sensitive gelatino-silver bromoiodide highly sensitive emulsion (the AgI content and the ratio of silver/gelatin were the same as in the First Layer) in a silver amount of 25 mg/100 cm$^2$ and a magenta color coupler in a coupler amount of 5.3 mg/100 cm$^2$. (Thickness: 3μ)

Fourth Layer: Yellow filter layer

A layer provided by coating a gelatin containing yellow colloidal dispersion of silver in a silver amount of 2.5 mg/100 cm$^2$. (Thickness: 3μ)

Fifth Layer: Blue-sensitive silver halide emulsion layer

A layer provided by coating a gelatino-silver bromoiodide highly sensitive emulsion (the AgI content and the silver/gelatin ratio were the same as in the First Layer) in a silver amount of 20 mg/100 cm$^2$ and a yellow color coupler in a coupler amount of 9.8 mg/100 cm$^2$. (Thickness: 3μ)

Sixth Layer: Protective layer

A layer mainly comprising gelatin. (Thickness: 1.5μ)

* Thickness means dry thickness.

The couplers for the First Layer, the Third Layer and the Fifth Layer were each dissolved in tricresyl phosphate, and emulsified and dispersed in gelatin for use.

To each of the First, Layer, the Third Layer and the Fifth Layer was added 4-hydroxy-6-methyl-1,3,3a,7-tetrazaindene as a stabilizer in an amount of 20 mg/m$^2$, and to the First Layer to the Fifth Layer were added sodium dodecylbenzenesulfonate as a coating aid, and triacryloylhexahydrotriazine as a hardener in an amount of 6 mg/m$^2$.

The following couplers were used as the cyan color coupler, the magenta color coupler and the yellow color coupler.

Cyan Coupler: 1-Hydroxy-N-[γ-(2,4-di-tert-amylphenoxypropyl)]-2-naphthamide

Magenta Coupler: 1-(2,4,6-Trichlorophenyl)-3-[3-(2,4-di-tert-amylphenoxyacetamido)benzamido]-5-pyrazolone Yellow Coupler: The same yellow coupler as described in Example 3.

Present Invention Sample (viii)

Sample (viii) of the present invention was prepared in the same manner as Sample (vii) using an emulsion prepared by dissolving Color Fog-Preventing Agent (1) described above together with the yellow color coupler in tricresyl phosphate and emulsifying and dispersing the mixture in gelatin as an, emulsion for the blue-sensitive silver halide emulsion layer (Fifth Layer). Color Fog-Preventing Agent (1) was added so as to be coated in an amount of 0.4 mg/100 cm$^2$.

Sample (ix) (for comparison)

Color Fog-Preventing Agent (3) described above was used in place of Color Fog-Preventing Agent (1) in Sample (viii).

Sample (x) (for comparison)

Color Fog-Preventing Agent (4) described above was used in place of Color Fog-Preventing Agent (1) in Sample (viii).

Sample (xi) (for comparison)

Color Fog-Preventing Agent (5) described above was used in place of Color Fog-Preventing Agent (1) in Sample (viii).

Samples (vii) to (xi) were stepwise exposed using white light, and development-processed according to the following color negative processing.

| Processing Step | Temperature | Time |
|---|---|---|
| Color Development | 38° C. | 3 min 15 sec |
| Stopping | " | 1 min |
| Washing | " | 1 min |
| Bleaching | " | 2 min |
| Washing | " | 1 min |
| Fixing | " | 2 min |
| Washing | " | 1 min |
| Stabilizing Bath | " | 1 min |

The processing solutions used had the following compositions.

| Color Developer | | |
|---|---|---|
| Sodium Hydroxide | 2 | g |
| Sodium Sulfite | 2 | g |
| Potassium Bromide | 0.4 | g |
| Sodium Chloride | 1 | g |
| Borax | 4 | g |
| Hydroxylamine Sulfate | 2 | g |
| Disodium Ethylenediaminetetraacetate (dihydrate) | 2 | g |
| 4-Amino-3-methyl-N-ethyl-N-(β-hydroxyethyl)aniline Monosulfate | 4 | g |

| -continued | | |
|---|---|---|
| Color Developer | | |
| Water to make the total | 1 | l |

| Stopping Solution | |
|---|---|
| Sodium Thiosulfate | 10 g |
| Ammonium Thiosulfate (70% aq. soln.) | 30 ml |
| Acetic Acid | 30 ml |
| Sodium Acetate | 5 g |
| Potassium Alum | 15 g |
| Water to make the total | 1 l |

| Bleaching Bath | |
|---|---|
| Fe(III)-Sodium Ethylenediaminetetraacetate (dihydrate) | 100 g |
| Potassium Bromide | 50 g |
| Ammonium Nitrate | 50 g |
| Boric Acid | 5 g |
| Aqueous Ammonia | to adjust pH to 5.0 |
| Water to make the total | 1 l |

| Fixing Solution | |
|---|---|
| Sodium Thiosulfate | 150 g |
| Sodium Sulfite | 15 g |
| Borax | 12 g |
| Glacial Acetic Acid | 15 ml |
| Potassium Alum | 20 g |
| Water to make the total | 1 l |

| Stabilizing Solution | |
|---|---|
| Boric Acid | 5 g |
| Sodium Citrate | 5 g |
| Sodium Metaborate (tetrahydrate) | 3 g |
| Potassium Alum | 15 g |
| Water to make the total | 1 l |

The yellow density (Y) in the unexposed areas of the thus-processed and dried samples was measured using a Fuji Model FAD automatic densitometer. The results obtained are shown in Table 3 below.

Table 3

| | Sample | | | | |
|---|---|---|---|---|---|
| | (vii) | (viii) | (ix) | (x) | (xi) |
| Yellow Density (Y) | 0.23 | 0.13 | 0.15 | 0.19 | 0.17 |

From the results, it was found that less color fog occurred with Sample (viii) containing the color fog-preventing agent of the present invention, thus showing the effectiveness of the present invention.

Precipitation of crystals occurred in Samples (ix) to (xi) using color fog-preventing agents outside the scope of the present invention either before or after coating. On the other hand, no precipitation of crystals was observed with Sample (viii) in accordance with the present invention.

EXAMPLE 6

A transparent polyethylene terephthalate film support was coated, in sequence, with the following layers to prepare Light-Sensitive Sheet I.

(1) An image-receiving layer comprising 3.0 g/m² of copoly[styrene-N-vinylbenzyl-N,N,N-trihexylammonium chloride] and 3.0 g/m² of gelatin.

(2) A white reflective layer comprising 18 g/m² of titanium dioxide and 1.8 g/m² of gelatin.

(3) An opaque layer comprising 2.5 g/m² of carbon black and 2.5 g/m² of gelatin.

(4) A layer comprising 0.5 g/m² of a cyan dye-releasing redox compound having the following formula

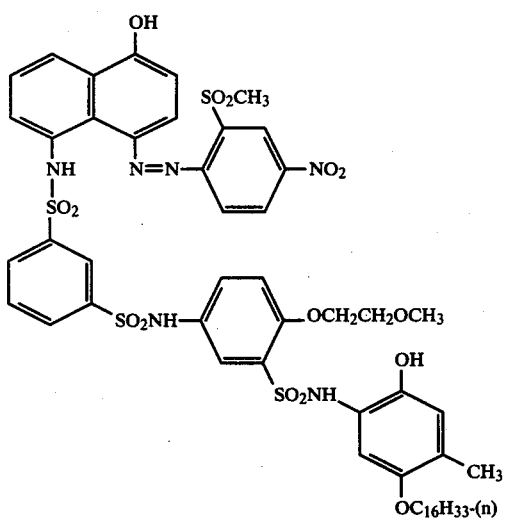

0.10 g/m² of N,N-diethyllaurylamide and 1.2 g/m² of gelatin.

(5) A layer comprising a red-sensitive internal latent image type silver iodobromide emulsion (containing 1.5 mol% of silver iodide, 1.1 g/m² of gelatin and 1.4 g/m² of silver), 0.015 g/m² of 1-acetyl-2-[4-(2,4-di-t-pentyl-phenoxyacetamido)phenyl]hydrazine and 0.067 g/m² of sodium 2-pentadecylhydroquinone-5-sulfonate.

(6) An interlayer comprising 1.6 g/m² of the hydroquinone compound substituted with two alkyl groups having 15 carbon atoms synthesized as described in Synthesis Example 1 (a mixture of isomers), 0.8 g/m² of tricresyl phosphate and 1.6 g/m² of gelatin.

As comparison samples to Light-Sensitive Sheet I, Light-Sensitive Sheet II in which 1.0 g/m² of 2,5-di-t-octyl hydroquinone as described in U.S. Pat. No. 2,008,032 was used in place of 1.6 g/m² of the hydroquinone compound according to the present invention and Light-Sensitive Sheet III in which 1.3 g/m² of 2,5-di-sec-dodecyl hydroquinone as described in U.S. Pat. No. 3,700,453 was used in place of 1.6 g/m² of the hydroquinone compound according to the present invention were prepared.

On a transparent polyethylene terephthalate film support were coated, in sequence, the following layers to prepare a cover sheet.

(1) A neutralizing layer comprising 10 g/m² of polyacrylic acid.

(2) A timing layer comprising 10 g/m² of cellulose acetate.

The following components were mixed to prepare a processing solution.

| | |
|---|---|
| Potassium Hydroxide | 56 g |
| t-Butylhydroquinone | 0.2 g |
| 4-Hydroxymethyl-4-methyl-1-phenyl-3-pyrazolidone | 8 g |

| -continued | |
|---|---|
| 5-Methylbenzotriazole | 2.4 g |
| Carbon Black | 40 g |
| Hydroxyethyl Cellulose | 25 g |
| Distilled water to make the total | 1,000 ml |

The above-described light-sensitive sheet was exposed through a gray wedge (8 CMS), and the above-described processing solution was spread, in a thickness of 85μ, between the above-described cover sheet and layer (6) of the light-sensitive sheet.

After 1 hour, the density of the color image transferred to the image-receiving layer was measured using a color densitometer. The results obtained are shown in Table 4 below.

Table 4

| Sample | Green Density at a Red Density of 1.0 |
|---|---|
| Light-Sensitive Sheet I* | 0.36 |
| Light-Sensitive Sheet II** | 0.55 |
| Light-Sensitive Sheet III** | 0.49 |
| Sample***Dyed with Cyan Dye | 0.33 |

*Invention
**Comparison
***Control

The smaller is the value of the green density/red density, the more desirable is the cyan hue.

From the results in Table 4, it can be seen that in Light-Sensitive Sheet I using the hydroquinone compound according to the present invention the value of the green density at a red density of 1.0 closely resembled that of the sample dyed with the cyan dye in comparison with those of Light-Sensitive Sheets II and III for comparison.

The sample dyed with the cyan dye was prepared by immersing a sample having coated on a support the above-described layers (1) to (3) of this example in a solution containing the following cyan dye dissolved in a 0.1 N sodium hydroxide aqueous solution.

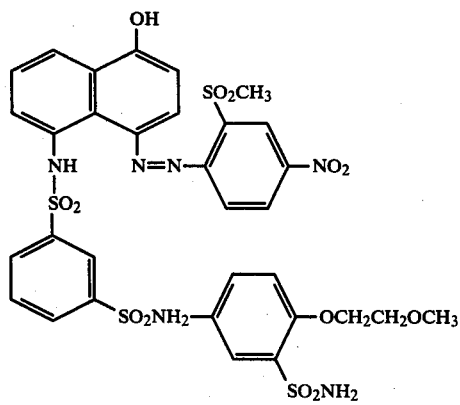

EXAMPLE 7

A transparent polyethylene terephthalate film support was coated, in sequence, with the following layers to prepare a light-sensitive sheet.

(1) to (5) Same as layers (1) to (5) described in Example 6.

(6) Same as layer (6) described in Example 6 except that the tricresyl phosphate was not present.

(7) A layer comprising 1.02 g/m² of the magenta dye-releasing redox compound having the following formula

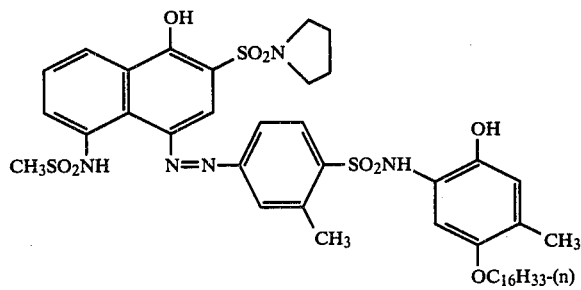

0.21 g/m² of N,N-diethyllaurylamide and 1.14 g/m² of gelatin.

(8) A layer comprising a green-sensitive internal latent image type silver iodobromide emulsion (containing 1.5 mol% of silver iodide, 1.1 g/m² of gelatin, 1.4 g/m² of silver), 0.015 g/m² of 1-acetyl-2-[4-(2,4-di-t-pentylphenoxyacetamido)phenyl]hydrazine and 0.067 g/m² of sodium 2-pentadecylhydroquinone-5-sulfonate.

(9) Same as layer (6) above.

(10) A layer comprising 1.01 g/m² of the yellow dye-releasing redox compound of the following formula

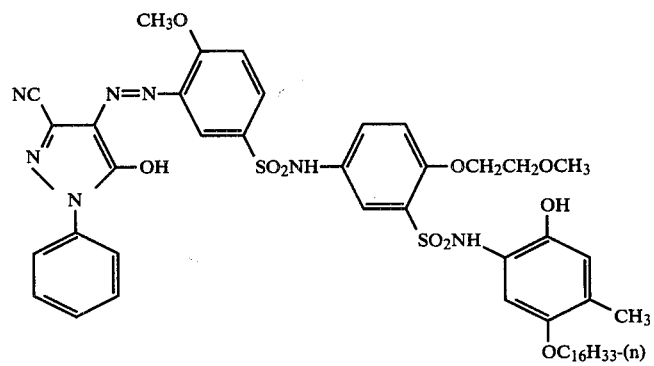

0.83 g/m² of N,N-diethyllaurylamide and 1.09 g/m² of gelatin.

(11) A layer comprising a blue-sensitive internal latent image type silver iodobromide emulsion (containing 1.5 mol% of silver iodide, 1.1 g/m² of gelatin, 1.4 g/m² of silver), 0.015 g/m² of 1-acetyl-2-[4-(2,4-di-t-pentylphenoxyacetamido)-phenyl]hydrazine and 0.067 g/m² of sodium 2-pentadecylhydroquinone-5-sulfonate.

(12) A layer of 1.3 g/m² of gelatin.

The above-described light-sensitive sheet was exposed through a multi-color wedge (8 CMS), and a processing solution as described in Example 6 was spread, in a thickness of 85μ, between the cover sheet as described in Example 6 and layer (12) of the light-sensitive sheet. After 15 minutes, a good multi-color image was observed through the support of the light-sensitive sheet.

While the invention has been described in detail and with reference to specific embodiments thereof, it will be apparent to one skilled in the art that various changes and modifications can be made therein without departing from the spirit and scope thereof.

What is claimed is:

1. A color photographic light-sensitive material comprising a support having thereon at least one layer of a silver halide photographic emulsion with the light-sensitive material containing at least one liquid hydroquinone compound substituted with one or two tertiary alkyl groups having 15 carbon atoms, or a precursor thereof, wherein said tertiary alkyl groups individually have 15 carbon atoms.

2. The color photographic light-sensitive material as claimed in claim 1, wherein the hydroquinone compound is the reaction product of hydroquinone with 3,7,11-trimethyldodecan-3-ol obtained in the presence of a Lewis acid.

3. The color photographic light-sensitive material as claimed in claim 1, wherein the hydroquinone compound is a mixture of isomers of a hydroquinone compound in which the 2- and 5-positions or the 2- and 6-positions of the benzene moiety are substituted with a tertiary alkyl group having 15 carbon atoms.

4. The color photographic light-sensitive material as claimed in claim 1, wherein the hydroquinone compound is represented by the following general formula (I):

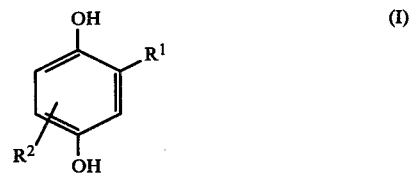

wherein $R^1$ represents a hydrogen atom,

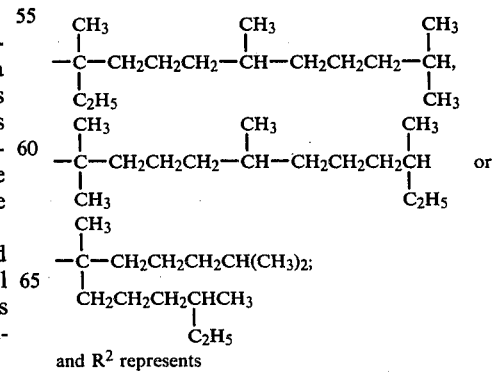

and $R^2$ represents

-continued

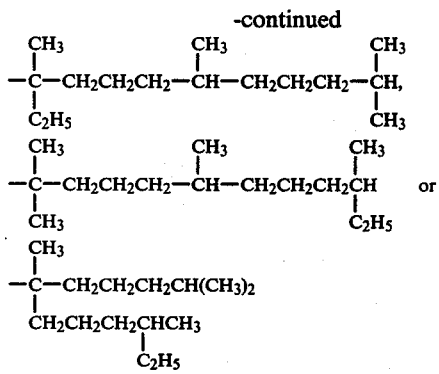

with R² being present in the 5- or 6-position of the benzene moiety when R¹ is not a hydrogen atom.

5. The color photographic light-sensitive material as claimed in claim 1, wherein the hydroquinone compound is 2,5-bis(1-ethyl-1,5,9-trimethyldecyl)hydroquinone.

6. The color photographic light-sensitive material as claimed in claim 1, wherein the hydroquinone compound is a mixture of 2,5-bis(1-ethyl-1,5,9-trimethyldecyl)hydroquinone and 2-(1-ethyl-1,5,9-trimethyldecyl)hydroquinone.

7. The color photographic light-sensitive material as claimed in claim 1, wherein the hydroquinone compound is present in a photographic emulsion layer or a layer adjacent thereto.

8. The color photographic light-sensitive material as claimed in claim 1, wherein the color photographic light-sensitive material further contains a dye image-providing compound.

9. The color photographic light-sensitive material as claimed in claim 8, wherein the hydroquinone compound is present in a layer containing the dye image-providing material in an amount of about 0.1 to about 150% by weight to the amount of the dye image-providing material.

10. The color photographic light-sensitive material as claimed in claim 9, wherein the hydroquinone compound is present in an amount of 0.2 to 20% by weight to the amount of the dye image-providing material.

11. The color photographic light-sensitive material as claimed in claim 8, wherein the hydroquinone compound is present in a layer other than a layer containing the dye image-providing material in an amount of about 1 to about 1,000% by weight to the amount of said dye image-providing material in said layer containing said dye image-providing material.

12. The color photographic light-sensitive material as claimed in claim 11, wherein the hydroquinone compound is present in an amount of 10 to 400% by weight to the amount of the dye image-providing material.

13. The color photographic light-sensitive material as claimed in claim 8, wherein said dye image-providing compound is a color-forming coupler or a diffusible dye-releasing redox compound.

14. The color photographic light-sensitive material as claimed in claim 8, wherein said light-sensitive material contains a red-sensitive silver halide emulsion layer containing a cyan color-forming coupler, a green-sensitive silver halide emulsion layer containing a magenta color-forming coupler and a blue-sensitive silver halide emulsion layer containing a yellow color-forming coupler.

15. The color photographic light-sensitive material as claimed in claim 8, wherein said light-sensitive material contains a layer containing a cyan dye-releasing redox compound, a red-sensitive silver halide emulsion layer, a layer containing a magenta dye-releasing redox compound, a green-sensitive silver halide emulsion layer, a layer containing a yellow dye-releasing redox compound and a blue-sensitive silver halide emulsion layer.

16. The color photographic light-sensitive material as claimed in claim 1, wherein all hydroquinone compounds present are liquid.

17. The color photographic light-sensitive material as claimed in claim 1, wherein only one liquid hydroquinone compound is present.

* * * * *